United States Patent [19]

Leverette

[11] Patent Number: 4,518,000

[45] Date of Patent: May 21, 1985

[54] DENTAL FLOSS APPLICATOR

[76] Inventor: Edward H. Leverette, 10014 S. Union, Chicago, Ill. 60628

[21] Appl. No.: 489,126

[22] Filed: Apr. 27, 1983

[51] Int. Cl.³ .............................................. A61C 15/00
[52] U.S. Cl. .................................................. 132/92 A
[58] Field of Search ...................... 132/92 R, 91, 92 A

[56] References Cited

U.S. PATENT DOCUMENTS

| | | | |
|---|---|---|---|
| 1,389,064 | 8/1921 | Martin ............................... | 132/92 R |
| 1,468,942 | 9/1923 | Gamble ............................. | 132/92 R |
| 2,381,530 | 8/1945 | Dembenski ........................ | 132/92 A |
| 3,340,881 | 9/1967 | Cowan .............................. | 132/92 R |
| 3,734,107 | 5/1973 | Thierman ......................... | 132/92 A |
| 4,178,947 | 12/1979 | McCourry ......................... | 132/92 R |
| 4,342,324 | 8/1982 | Sanderson ......................... | 132/92 R |

Primary Examiner—Gregory E. McNeill
Attorney, Agent, or Firm—Hill, Van Santen, Steadman & Simpson

[57] ABSTRACT

Dental floss applicator storing clean floss and taking in spent floss and holding the clean floss under tension for cleaning between the teeth without placing the hands in or near the mouth. Clean and used or spent floss are stored in separate compartments of a container, of a size to fit in the average hand. The container, is closed on its sides and one end and along its top and bottom and a hollow arm having separate passageways leads from the container and forms an end wall of the container. The hollow arm has a forked hollow end in which the tines terminate in the same plane and are spaced apart and hold a length of taut clean floss in the space between the ends of the tines.

A pay out reel containing a supply of floss rotatably mounted in the clean floss compartment and a take up reel for the spent floss is rotatably mounted in the spent floss compartment. The reels are indexed as manually turned after each flossing operation to provide a supply of taut clean floss positioned to facilitate flossing of the teeth without touching the floss or mouth by hand.

4 Claims, 5 Drawing Figures

U.S. Patent   May 21, 1985   4,518,000
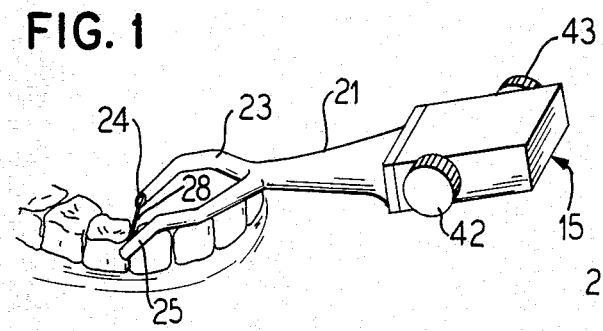
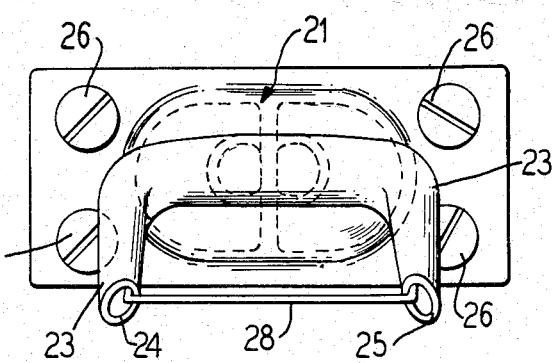
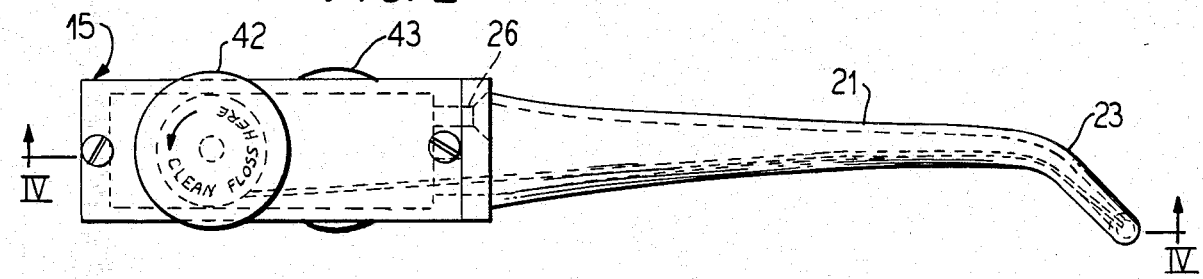
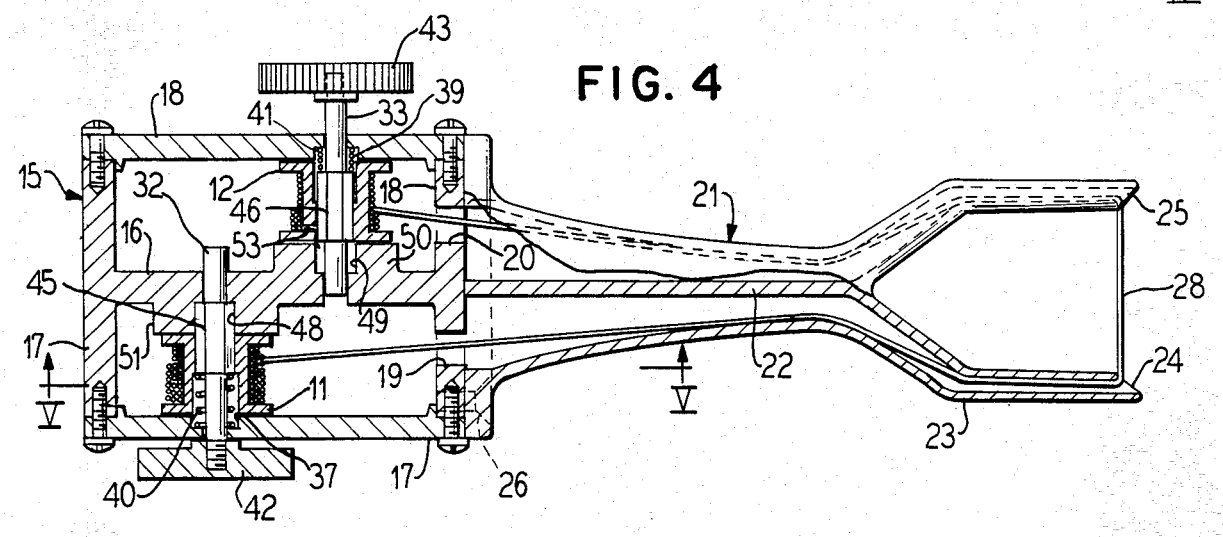
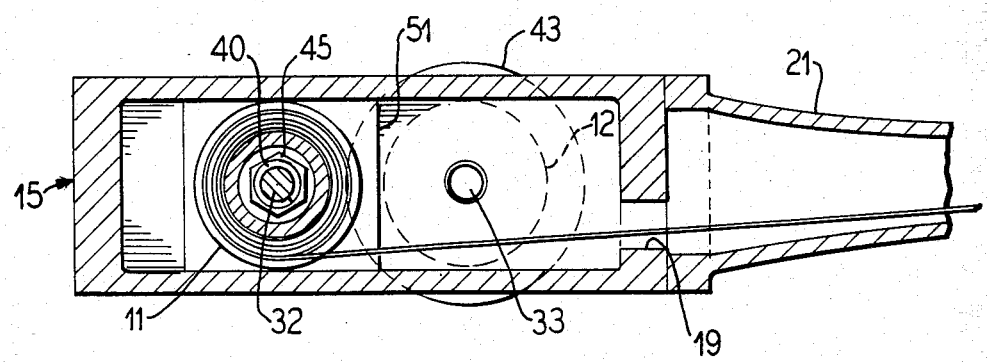

DENTAL FLOSS APPLICATOR

BACKGROUND OF THE INVENTION

Dental floss has heretofor been supplied on reels enclosed in a cylindrical or box-like container and has been payed off of the reel by hand and broken off for use by the two hands. The teeth are customarily flossed by grasping the ends of the floss by the hands and stretching the floss and moving a strip of floss back and forth between the teeth. The used or spent floss must be thrown away. It is difficult to grasp and stretch the floss and hold the floss tight without twisting the floss around the finger of each hand. This type of flossing operation is not only clumsy but is unduly wasteful and unsanitary since the floss wrapped around the fingers of each hand and stretched for insertion between the teeth and then broken off is subject to dirt from the hands, or other sources, such as the particles between the teeth, and must be discarded after each flossing operation.

SUMMARY OF THE INVENTION

In accordance with the principles of the present invention a container separating clean and spent floss is provided which is of a size fitting the average hand.

A clean floss reel is provided in a clean floss compartment of the container, and a spent floss reel is provided in a spent or used floss compartment in the container. A hollow arm extends from an end wall of the compartment and is separated into clean and spent floss passageways and terminates in a bifurcated end, the furcations of which are hollow and terminate in the same plane, and open toward each other, to accommodate the floss to be trained from the clean floss compartment across the space between the furcations of the bifurcated arm and wound on the spent floss reel in the spent floss compartment in increments required to supply a predetermined amount of clean, taut floss between the furcations of the arm. The floss is payed off in increments, which may be in the order of one inch for each flossing operation. This is attained by slidably keying the reels in the container, and biasing the keying members to enter a socket in an intermediate wall of the container, conforming to the key and moving one keying member against its bias out of the socket, and turning the keying member and spent floss reel by hand as the clean floss keying member is manually moved out of its socket to accommodate clean floss to be paid from its reel and stretched across the furcations of the end portion of the hollow arm.

An object of the present invention is to provide an applicator for floss, holding the floss for flossing between the teeth, which is of simple construction and more convenient to use than the floss supplied in conventional containers in which the floss must be broken off for use and discarded upon completion of the flossing operation.

A further object of the invention is to provide a floss applicator for the application of floss between the teeth, which may readily be held by the hand and will fit in the average mouth, to be moved back and forth between the teeth, to minimize the waste of floss and make it more convenient to floss the teeth.

A still further object of the invention is to provide a sanitary simplified floss applicator, which will readily fit in the hand and maintain the floss taut as the teeth are flossed, and which accurately supplies a predetermined amount of floss for each flossing operation.

An average of the invention is that flossing may be attained without placing either hand in the mouth, and a predetermined amount of clean taut floss is always available.

A further advantage of the invention is in the provision of a positive feeding means for reeling out a predetermined amount of clean floss from a clean floss reel and taking in the used or spent floss, and maintaining the floss taut for flossing the teeth, and thereby avoiding the waste and contamination of floss present in the common methods of flossing the teeth.

These and other objects and advantages of the invention will appear from time to time as the following specification proceeds, and with reference to the accompanying drawings wherein:

BRIEF DESCRIPTION OF THE DRAWINGS

FIG. 1 is a diagrammatic perspective view of the flossing applicator of the present invention, illustrating the application of floss between the teeth, but only showing a few lower teeth of the jaw and not showing the mouth or hands of the person, operating the applicator, for simplicity in illustrating the invention.

FIG. 2 is a side elavational view of the floss applicator shown in FIG. 1.

FIG. 3 is an end view of the floss applicator shown in FIGS. 1 and 2, looking at the applicator from the floss applying end thereof.

FIG. 4 is a horizontal sectional view taken through the floss applicator along line IV—IV of FIG. 2, with certain parts of the floss applying arm shown in plan; and FIG. 5 is a longitudinal sectional view taken substantially along line V—V of FIG. 4.

DESCRIPTION OF THE PREFERRED EMBODIMENT

In the embodiment of the invention illustrated in the drawings, I have shown a dental floss applicator adapted to apply clean taut floss, to clean between the teeth, and to store sufficient floss in a clean floss reel 11 to last for a period of approximately one year as spent floss is drawn onto a spent floss reel 12.

The floss applicator generally includes a container 15 having an intermediate wall 16 separating the reels 11 and 12 to assure a supply of clean floss which will not be contaminated by the spent or dirty floss. The container 15 may be of a size which will readily fit in the palm of an average hand and is herein shown as being rectangular in form, but may be of other suitable forms which will conveniently fit in the palm of the hand.

The interior portion of the container is separated by the intermediate wall 16, shown as being formed from a member of a generally H shaped form with one leg of the H forming an end closure wall 17 for the container, and the other leg of the H forming an opposite wall 18 of the container, and having apertured portions 19 and 20 leading therethrough. The top and bottom walls of the container, may be formed integrally with the H shaped member forming the intermediate wall 16.

The apertured portion 19 leads from the clean compartment of the container and the apertured portion 20 leads into the spent floss compartment of the container, to accommodate the used floss to be wound on the reel 12. The outer side of the leg of the H forming the end wall and the apertured portions 19 and 20 leading therefrom and thereinto respectively, form a mounting for a hollow arm 21 having a central divider wall 22 terminating into a generally Y shaped portion forming a bifurcated end portion 23 of the arm, the furcations of which terminate into open ends 24 and 25. The open ends extend at opposite angles with respect to each other to face each other and accommodate the floss to be stretched across the space between the open ends 24 and 25 and pass back along the hollow arm 21 to the reel 12 upon which the spent floss is taken up.

The hollow arm 20 may be secured to the ends of the side walls 17 and 18 of the container as by machine screws 26 or other suitable securing devices, which mount the arm 21 on the container 15, in abutting engagement with the ends of the wall 17 to ridgedly extend therefrom and accommodate the floss to be stretched taut across the furcations of the bifurcated end portion of the arm 21, as indicated by references numeral 28 in FIGS. 1, 3 and 4.

The sidewalls 17 and 18 close opposite sides of the container and are apertured to receive parallel spaced shafts 32 and 33 for the respective reels 11 and 12, which rotatably and slidably extend therethrough. The innersides of the apertured portions of the sidewalls are enlarged to provide sockets 37 and 39 for springs 40 and 41 respectively, encircling the respective shafts 32 and 33. Said springs 40 and 41 form biasing springs biasing keys 45 and 46 respectively, on the respective shafts on which said keys are mounted to extend within said socket the respective socket 48 and 49.

The shafts 32 and 33 have threaded outer ends to receive knobs 42 and 43 for respective of said shafts to axially move either of the shafts 32 or 33 and the respective keys 45 and 46 thereon out of the respective sockets 48 and 49 in the divider wall 16 and to accommodate turning of the respective shafts 32 and 33 and the reels thereon in a direction to wind spent floss on the spent floss take-up reel 12 and to accommodate clean floss to be paid out from the clean floss reel 11 in increments sufficient to supply taut clean floss between the open ends 24 and 25 of the furcations of the bifurcated portion of the arm 21, for application between the teeth.

The respective sockets 48 and 49 are formed in bosses 50 and 51 on opposite sides of the divider wall 16. As shown in FIG. 5, the keys 45 and 46 may be of a hexagonal form in end view and are keyed or otherwise secured to the respective shafts 32 and 33 to move therewith in all axial positions of said shafts. The interior portions of the reels 11 and 12 are also formed to fit the respective keys 45 and 46 to enable each key to hold its shaft 32 or 33 and reel 11 and 12 from rotation as the respective reel 12 and shaft 33 turned by turning movement of knob 43 on the end of the shaft 33.

The key 46 is shown in FIG. 4 as moved out of the socket 49 in the divider 16 by pulling outwardly on the knob 43, to accommodate turning movement of the spent floss take-up reel 12 by turning movement of said knob 43.

During flossing of the teeth, the keys 45 and 46 are both engaged in the respective keyways forming the walls of the sockets 48 and 49 by the respective compression springs 40 and 41, to hold the reels 11 and 12 from turning movement, and hold the floss taut across the open ends of the fractions 24 and 25 of the hollow arm 21, as indicated by reference numeral 28 in FIGS. 1, 3, and 4. It should here by understood that the walls of the sockets 48 and 49 correspond to the keys 45 and 46 with sufficient clearance to accommodate the keys to slidably move thereinto by the bias of the respective springs 40 and 41, and be removed therefrom against the bias of the respective springs 40 and 41.

When it is desired to supply clean floss, in the space between the furcations 24 and 25, the keys 45 and 46 should be withdrawn from their respective socket 48 and 49. At this time the key 45 being out of engagement with its socket, turning of the knob 43, will pay clean floss from the clean floss reel 11 and takeup spent or dirty floss on the spent floss reel 12.

When clean floss is taut between the opening 24 and 25, the hand may be removed from the knob 42 and the key will be turned by the reel 11 as floss is payed from the reel until it mates with the faces of the keyway formed by the socket 48. The spring 40 will then engage the key 45 with its socket and the reel 11 will be held from rotation.

As the hand is removed from the knob 43, the key 46 will also be biased into engagement with its socket 49 by the spring 41.

Each key 45 and 46 is shown as being hexagonal in form, as previously mentioned, and the respective sockets 48 and 49 are of a similar form. The hex faces of the keys 45 and 46 are of such a length in comparison with the diameters of the reels 11 and 12 as to measure $2\frac{1}{2}$ centimeters of floss between the furcations 24 and 25 of the bifurcated end of a hollow arm 21, for each face of the key 46. Since the effective diameter of the reel 12 increases as floss is wound on the reel, it is of advantage to turn the reel 12 more than one face of the key when initially bringing floss between the open ends 24 and 25 of the furcations or times of the bifurcated arm 23, and that the amount of turning of the two reels, while definite when the take up reel is empty, may be varied as the take up reel increases in circumference due to the increasing amount of floss in this reel. The amount of turning to supply the correct amount of taut floss for flossing may be a matter of experiment when initially starting a flossing operation.

It should be further understood that the faces of the keys 45 and 46 need not be the faces of a hexagon, but may be the faces of an octagon, or any other preselected polyhedron to account for differing circumferences of the reels as floss is payed from one reel and taken up on another and assure a supply of taut floss for each flossing operation.

Other forms of measuring means, such as pawls and ratchets, may also be used in place of fixed keys and keyways without departing from the spirit and scope of the novel concepts of the invention.

It has been found that if the clean floss reel 11 when initially inserted along its keyways contains 30 yards of floss and the distance the floss is stretched between the furcations 24 and 25 is approximately one inch, that the floss on a clean floss reel will last for substantially one year and that the reels need only be replenished and emptied about once a year.

It should be further be observed from FIG. 4 that when the floss is first trained onto the spent floss reel 12, it passes through the hole 53 in the reel and is clamped between the inner flange of the reel and the key 46. This is to assure winding of the spent floss on its reel and maintain the floss taut between the furcations 24 and 25.

I claim as my invention:

1. For use in storing and holding dental floss taut to be applied between the teeth for a flossing operation and advancing the spent floss to provide a fresh supply of clean floss for a next succeeding flossing operation, a generally hollow container of a size conveniently fitting the hand of an average individual and having a longitudinally extending interior wall separating the container into a clean floss compartment and a spent floss compartment, said container having one closed end wall and an opposite end wall having spaced passageways leading therethrough, a hollow arm leading from the passageways leading through the opposite end wall and having separate passaageways leading from and to said last mentioned passageways, said hollow arm having bifurcated end, in which the furcations thereof extend generally parallel and terminate in the same plane, to accommodate clean floss to be stretched thereacross, a pay-out reel in said clean floss compartment, a take-up reel in said spent floss compartment operable independently or simultaneously of said pay-out reel, whereby clean floss may be paid from said clean floss compartment and along an associated passageway in said end wall to and along an outlet passageway in said hollow arm and along a furcation thereof and across said furcations of said hollow arm and inwardly along the opposite furcation and be wound on said take-up reel and maintained taut across said furcations by cooperation between said take-up reel and said clean floss reel, an individual transverse shaft for each reel extending across said casing and rotatably and translationally mounted at their inner ends in said interior wall and extending outwardly of said casing out the outer side walls thereof, keying sockets for said shafts in said inner wall, keying member intermediate the ends of said shafts, movable within said sockets and having slidable and keying engagement with the interior portions of said reels, spring means biasing said shafts into engagement with said sockets to hold said shafts from rotation, and means selectively operable from the exterior of said container to independently translationally or rotatably move either of said shafts to effect indexing of said shafts to hold said reels from rotation or independently release either or both of said keying members from said sockets to attain independent rotatable movement of either of said shafts and supply and maintain taut clean floss across the 2. The apparatus of claim 1 in which said indexing means are keying members on said shafts intermediate the ends thereof and cooperate with keying sockets on opposite sides of said interior walls, and in which compression springs encircle said shafts and bias said keying members into engagement with said sockets to hold said reels from rotation, and knobs on the outer ends of said shafts are effective to independently move said keying members out of engagement with said sockets against the bias of said springs to accommodate rotation of said selected reels by knobs on the outer ends of said shafts.

3. The floss applicator of claim 5 in which the keying members have polyhedral faces extending for the length thereof, each face being the same as the other to index rotation of said reels and to hold either or both of said reels from rotation upon the supply of a measured amount of clean taut floss in the space between the furcations of said bifurcated arm for a flossing operation.

4. The floss applicator of claim 3 of which the polyhedral faces of said keying members are hexagonal, and the reels are so proportioned as to effect the indexing of the take-up reel to advance a predetermined amount of clean floss as spent floss is wound onto said take-up reel.

* * * * *